United States Patent [19]

Pronovost et al.

[11] Patent Number: 5,234,817
[45] Date of Patent: Aug. 10, 1993

[54] WASH SOLUTION CONTAINING A CATIONIC SURFACTANT AND ITS USE IN CHLAMYDIAL AND GONOCOCCAL DETERMINATIONS

[75] Inventors: Allan D. Pronovost, San Diego; James H. Gilbert, Oakland, both of Calif.

[73] Assignee: Eastman Kodak Company, Rochester, N.Y.

[21] Appl. No.: 709,677

[22] Filed: Jun. 3, 1991

Related U.S. Application Data

[62] Division of Ser. No. 255,924, Oct. 7, 1988, Pat. No. 5,047,325.

[51] Int. Cl.$^5$ .................... C12Q 1/00; G01N 33/53
[52] U.S. Cl. .................... 435/7.36; 252/89.1; 252/110; 252/351; 514/642; 514/643
[58] Field of Search ............... 435/7.36; 514/642, 643; 252/89.1, 110, 351

[56] References Cited

U.S. PATENT DOCUMENTS

| | | | |
|---|---|---|---|
| 2,479,850 | 8/1949 | Marks | 514/643 |
| 2,786,797 | 3/1957 | Lederer | 514/642 |
| 3,856,684 | 12/1974 | Atkinson | 252/547 |
| 4,241,045 | 12/1980 | Gaafar . | |
| 4,331,447 | 5/1982 | Kamada et al. . | |
| 4,497,899 | 2/1985 | Armstrong et al. . | |
| 4,497,900 | 2/1985 | Abram et al. . | |
| 5,055,219 | 10/1991 | Smith | 252/547 |

FOREIGN PATENT DOCUMENTS

| | | |
|---|---|---|
| 174106 | 8/1985 | European Pat. Off. . |
| 264036 | 10/1987 | European Pat. Off. . |
| 58-187862 | 11/1983 | Japan . |

OTHER PUBLICATIONS

Szewczyk et al.–Chem. Abst. vol. 103 (1985) pp. 210, 309d.
Wahl et al.–Chem. Abst. vol. 106 (1987) p. 81234m.
Caldwell et al, *J. Clin. Microbiol.*, 18(3); pp. 539–545 (1983).

*Primary Examiner*—Sam Rosen
*Attorney, Agent, or Firm*—J. Lanny Tucker

[57] ABSTRACT

A wash solution having a pH of from about 7 to about 12 comprises at least about 0.1 weight percent of one or more cationic surfactants. This wash solution is useful in assays for chlamydial or gonococcal organisms, such as *Chlamydia trachomatis* or *Neisseria gonorrhoeae*. In particular, it can be used to remove uncomplexed materials from the insolubilized complexes formed between antigen and antibodies.

3 Claims, No Drawings

WASH SOLUTION CONTAINING A CATIONIC SURFACTANT AND ITS USE IN CHLAMYDIAL AND GONOCOCCAL DETERMINATIONS

REFERENCE TO RELATED APPLICATION

This application is a divisional of U.S. Ser. No. 07/255,924 filed Oct. 7, 1988, now U.S. Pat. No. 5,047,325.

FIELD OF THE INVENTION

The present invention relates to a wash solution useful in the determination of chlamydial or gonococcal organisms in a biological specimen. In particular, this invention relates to a wash solution which comprises a cationic surfactant.

BACKGROUND OF THE INVENTION

Immunoassays have been used in recent years to detect the presence of infectious diseases. In order for the assay to be useful, it must detect a particular organism with a high degree of reliability. In most cases, this requires the isolation and reaction of antigens peculiar to the organism with corresponding antibodies. For the test to be commercially successful, it also needs to be relatively inexpensive, simple to use and rapid.

One such organism which can be detected by immunoassay is *Chlamydia trachomatis* (herein *C. trachomatis*) which is one of two microbial species of the genus Chlamydiaceae, order Chlamydiales. There are 15 or more strains of this species which are the causes of a number of human ocular and genital diseases including trachoma, inclusion conjunctivitis, lymphogranuloma venereum, nongonococcal urethritis and proctitis. Infection from *C. trachomatis* is pervasive in the general population so that it is believed that there are millions of cases each year of nongonococcal urethritis alone.

Gonorrhea is a disease usually transmitted by sexual contact caused by a bacterium of the Neisseria genus, especially *N. gonorrhoeae*. The disease has plagued mankind for thousands of years, and although antibiotics have helped control its spread, it still persists in epidemic proportions in many parts of the world. The importance of detection and treatment of this organism is well recognized. *N. meningitidis* and *N. lactamica* are also species of considerable medical and diagnostic interest.

Because of the widespread nature of these diseases, there is considerable interest in having a rapid, simple and reliable test for detection of chlamydial and gonococcal organisms. Considerable research has been carried out to find useful ways to extract detectable antigen from chlamydial organisms. See for example, U.S. Pat. Nos. 4,427,782 (issued Jan. 24, 1984 to Caldwell et al) and 4,663,291 (issued May 5, 1987 to Rose) and E. P. Publications 174,106 (Becton) and 193,431 (Caldwell et al).

Assays for *C. trachomatis* and *N. gonorrhoeae* carried out using a solid support are described in U.S. Pat. Nos. 4,497,899 and 4,497,900, respectively (both issued Feb. 5, 1985 to Armstrong et al and Abram et al, respectively). The described assays are performed by extracting antigen from the organism and coating it on a bare solid support. The coated antigen is then detected with either one or two antibodies, one of which is suitably labeled. The critical feature of the assays appears to be the use of a solid support for attachment which is untreated or uncoated with material. Attachment of antigen is apparently achieved by incubating the coated support for an extended time sufficient to cause adsorption of antigen thereon (Col. 2, lines 51-55 of U.S. Pat. No. 4,497,899). The entire assay described in U.S. Pat. No. 4,497,899 takes at least 3 hours to perform. A similar but somewhat quicker assay is described in U.S. Pat. No. 4,497,900 for *N. gonorrhoeae* (see Cols. 4 and 5).

In the practice of these known assays, bound antigen and bound immunological complexes are washed with water or a buffer. Caldwell et al [*J. Clin. Microbiol.*, 18(3), pp. 539-545, 1983] describe an immunoassay for *C. trachomatis* in which wash steps were carried out using a phosphate buffered saline solution containing a nonionic surfactant, Tween TM 20. A similar assay for *N. gonorrhoeae* antibodies is described in U.S. Pat. No. 4,241,045 (issued Dec. 23, 1980 to Gaafar).

Use of known washing procedures in assays for chlamydial or gonococcal organisms is unacceptable because the background is too high or the sensitivity is too low and antibodies are found to bind to the solid supports rather than to antigen.

SUMMARY OF THE INVENTION

The problems noted above are overcome with a wash solution having a pH of from about 7 to about 12 and at least about 0.1 weight percent of one or more cationic surfactants.

This invention also provides a method for the determination of chlamydial or gonococcal organisms comprising:

A. contacting chlamydial or gonococcal antigen extracted from a specimen suspected of containing chlamydial or gonococcal organisms, respectively, with an antibody to the antigen so as to form an immunological complex of the antigen and antibody, B. prior to, simultaneously with or subsequent to complex formation, insolubilizing either or both of the antigen or antibody on a solid support so as to form a bound immunological complex, C. separating uncomplexed materials from the bound immunological complex by washing the complex with a wash solution having a pH of from about 7 to about 12 and at least about 0.1 weight percent of one or more cationic surfactants, and D. determining the presence of the bound complex as an indication of the amount of chlamydial or gonococcal organisms in the specimen.

The assay of this invention is rapid, reliable and simple to use. For example, it can be carried out in less than 30 minutes at room temperature. It is highly reliable for detecting extracted chlamydial antigen (such as *C. trachomatis*), and particularly the lipopolysaccharide antigen. It can also be used to rapidly and sensitively detect a gonococcal antigen (such as *N. gonorrhoeae*).

The assay is highly sensitive, shows low background, and negatively-charged substances which might interfere have little effect. Moreover, undesired binding of antibodies to the solid support in the assay is minimized. These advantages are achieved in the present invention from the use of a wash solution which contains a cationic surfactant and which has a pH of from about 7 to about 12. This wash solution is used at least once in the assay, that is, normally after formation of antibody-antigen immunological complex bound to the solid support. Preferably, the wash solution is used whenever washing is needed, a multiplicity of times if desired.

DETAILED DESCRIPTION OF THE INVENTION

The present invention is a method for determining the presence of *C. trachomatis* (or other chlamydial species), or the presence of *N. gonorrhoeae* (or other gonococcal species) in a biological specimen which has been obtained from a patient using any suitable medical or diagnostic techniques. Such specimens include, for example, swab specimens obtained from the cervix, urethra, throat or anus of a patient, and body fluids such as synovial fluid or fluid from lesions. The biological specimens so obtained are suspected of containing bacterial organisms which comprise the chlamydial or gonococcal antigen (or mixture thereof) to be determined.

While the assay can be carried out to detect antigenic sites of whole chlamydial or gonococcal cells, it is usually desirable to extract the antigens from the organisms in order to increase assay sensitivity. Standard techniques can be used for lysing the organism to release antigen including, for example, solvent dilution or high pH lysing solutions, enzyme treatment and physical agitation such as sonication or centrifugation. Heating is described as a lysing technique in E. P. Publication 183,383 (published Jun. 4, 1986). The use of anionic detergents or salts such as sodium dodecyl sulfate and deoxycholate is described in U.S. Pat. Nos. 4,497,899, 4,497,900 (both noted above) and 4,663,291 (issued May 5, 1987 to Rose).

In a preferred embodiment, the present invention can be used to detect the chlamydial lipopolysaccharide (glycolipid group) antigen (as described, for example, in E. P. Publication 193,431, published Sep. 3, 1986). Extraction procedures are also described therein. In another embodiment, the detected antigen can be the chlamydial major outer membrane protein of the organism which comprises about 60% of the total associated outer membrane protein. This antigen and methods of extraction are described in U.S. Pat. No. 4,427,782 (issued Jan. 24, 1984 to Caldwell et al). In some instances, a mixture of these chlamydial antigens will be detected using the present invention. In still other embodiments, the invention is used to detect one or more gonococcal antigens (IA or IB protein), or mixtures of antigens from individual gonococcal strains.

A preferred extraction composition is described in detail in copending and commonly assigned U.S. Ser. No. 255,928 filed on even date herewith by Pronovost, Mauck, Sullivan, Greer and Gilbert and entitled "High pH Extraction Composition and Its Use to Determine a Chlamydial, Gonococcal or Herpes Antigen". The central feature of that composition is the presence of an alcoholamine and its high pH (at least about 8). Further details of this preferred composition are provided below in relation to the examples.

In addition, it may be desirable to use a protease in the extraction procedure to break down whole blood and mucous. This is described in copending and commonly assigned U.S. Ser. No. 255,922 filed on even date herewith by Gilbert, Mauck and Stowers and entitled "Use of a Protease in the Extraction of Chlamydial, Gonococcal and Herpes Antigens".

Once antigen is extracted from the organism, it is desirable, although not essential, that the specimen be prefiltered to remove cell debris, particulate matter and other unwanted materials prior to further handling. Prefiltering can be carried out in a suitable container having a filter of some type.

Extraction can be carried out in any suitable container including devices specially designed for extraction of antigen. Useful devices are known in the art, including U.S. Pat. No. 4,746,614 (issued May 24, 1988 to Devaney, Jr. et al).

The extracted antigen is detected using an immunoassay in which it is immunologically reacted with one or more appropriate antibodies. The resulting immunological complex is detected using a suitable radiometric, colorimetric, fluorometric or enzyme labeled reagent. In some cases, the reagent is a labeled antibody to the antigen, and in other cases, the labeled anti-antibody is directed to an unlabeled antibody which is reactive with the antigen. Such immunoassays generally include the formation of a detectable immunological complex on a solid support of some type, either coated or uncoated, followed by appropriate detection procedures. Other assays involve agglutination of the immunological complex when at least one reactant (such as an antibody) of the complex is attached to labeled or unlabeled particles of some type that clump together during complex formation.

Examples of useful assays include competitive immunoassays or enzyme-linked immunoabsorbent assays (or what is commonly called "ELISA"). Such assays are described generally in U.S. Pat. No. 4,427,782 (noted above) and by Schmeer et al, *J. Clin. Microbiol.*, 15(5), pp. 830–834 (1982). The chlamydial or gonococcal antibodies used can be directed to either or several antigens being extracted from the organisms. In one embodiment, antibodies are directed to a single antigen, such as the lipopolysaccharide of the *C. trachomatis*. In other embodiments, a mixture of different antibodies is directed to several antigens, such as those extracted from several gonococcal strains.

Preferably, extracted antigen is contacted with a polymeric solid support to which it can become bound. Useful support materials include glass, cellulosic or polymeric beads, films, tubes, gels, plates and others known in the art. Preferably, the support material is a microporous membrane as described in more detail below. This membrane can be "bare", that is uncoated or untreated with any substance (as shown in U.S. Pat. No. 4,497,899, noted above). However, it can be treated or coated with a substance (such as a surfactant) which may enhance assay performance.

Copending and commonly assigned U.S. Ser. No. 255,923 filed on even date by Pronovost and entitled "Determination of a Chlamydial or Gonococcal Antigen Using a Positively-Charged Ionically Binding Support" describes solid supports which have a multiplicity of positively charged groups on the surface thereof. These positively charged groups produce a positive surface charge on the support, that is, a positive zeta potential over a wide pH range. Zeta potential is known as the potential between the support and a fluid in contact with it. Any positively charged chemical radical which produces the desired zeta potential on the support is useful in the practice of this invention.

For example, the support can be constructed of any natural or synthetic polymeric material with suitable cationic groups thereon which will ionically bind to the extracted antigen. Useful polymers include polyesters, polyamides, polyethyleneimines, polycarbonates, cellulosic materials, addition polymers prepared from ethylenically unsaturated vinyl monomers and others known in the art having the requisite charged groups. Generally, the cationic groups are quaternary ammonium salts, quaternary phosphonium salts, quaternary sulfonium salts, quaternary pyridinium salts, quaternary pyrimidinium salts or quaternary imidazolium salts. Quaternary ammonium salts are preferred. Further details can be obtained by consulting the application, incorporated herein by reference.

One useful polymeric solid support is a microporous membrane manufactured and sold by Pall Corp. as Posidyne® or Biodyne®-B membranes. These supports comprise a nylon membrane coated with a polyester which has quaternary ammonium groups in surfactant, are also useful in the practice of this invention.

In contrast to the embodiments described above wherein the antigen is bound to the solid support prior to immunological reaction, the assay of this invention can also be carried out by forming the immunological complex simultaneously with or prior to attachment to the solid support. In other words, the complex can be formed in solution followed by contact with the solid support for binding thereto.

The support described herein can be used in combination with other equipment (bottles, test tubes, swabs, beakers or cups) in order carry out the assay. Alternatively and preferably, the support is a microporous membrane which is fitted into a disposable test device in which the assay can be carried out and all fluids accommodated. Useful configurations of test devices are known in the art including U.S. Pat. Nos. 3,825,410 (issued Jul. 23, 1974 to Bagshawe), 3,888,629 (issued Jun. 10, 1975 to Bagshawe), 3,970,429 (issued Jul. 20, 1976 to Updike) and 4,446,232 (issued May, 1984 to Liotta). Particularly useful devices are described and claimed in copending and commonly assigned U.S. Ser. Nos. 19,810 (filed Feb. 27, 1987 by Hinckley) and 98,248 (filed Sep. 18, 1987 by Hinckley).

Almost immediately upon contact of the antigen with the support, the antigen is bound to the support. If desired, any unbound antigen may be removed from the support by washing with the wash solution of this invention.

Within about 10 minutes, and preferably within 1 to 5 minutes, of the contact, the bound antigen is contacted with chlamydial or gonococcal antibody so as to form an immunological complex on the support. Fluid and unbound materials can be removed quickly at the same time. If the assay is carried out using a disposable test device, the support can be a microporous membrane through which fluid and unbound materials in the specimen are allowed to flow through as the antigen is bound to the membrane.

The antibody used in this assay is specifically immunoreactive with one or more chlamydial or gonococcal strains (depending upon what organism is of interest). It can be polyclonal or monoclonal. If polyclonal, it is commercially available or prepared in various animals using known techniques employing an antigen common to the strain of organism to be detected. A single antibody or mixture thereof can be used. For example, antibody to either the chlamydial lipopolysaccharide or major outer membrane protein antigen, or antibodies to both antigens can be used in the assay. Preferably, the antibodies are monoclonal which are either commercially available or prepared using standard hybridoma technology. Useful procedures for preparing antibodies are described, for example, in E.P. Publication 193,431 and U.S. Pat. No. 4,427,782 (noted above).

In one embodiment, the antibody to the antigen is labeled for detection. Useful labels are known in the art and include chemical or biological compounds which are directly detectable using suitable procedures and equipment, as well as compounds which can be detected through further chemical or specific binding reactions to provide a detectable species. Examples of useful labels include radioisotopes, enzymes, fluorescent compounds, chemiluminescent compounds, phosphorescent compounds, biotin or its derivatives, avidin or its derivative, ferritin, magnetizable particles, dyed particles and others readily apparent to one skilled in the art. Radioisotopes or enzymes are preferred labels. The labels can be attached to antibodies using known techniques. Where the label is not directly detectable, further reagents or compounds are needed to render the reaction or specific binding product detectable. For example, if the label is biotin, it can be reacted with avidin which is conjugated with an enzyme to provide a detectable species. Where the label is an enzyme, such as glucose oxidase, urease, peroxidase, alkaline phosphatase and others, substrates and dye-providing reagents are also needed.

In a particularly preferred embodiment, the label is peroxidase, and at some point in the assay, hydrogen peroxide and suitable dye-forming reagents are added to provide a detectable dye. For example, useful dye-providing reagents include leuco dyes, such as triarylimidazole leuco dyes (as described in U.S. Pat. Nos. 4,089,747, issued May 16, 1978 to Bruschi), or other compounds which react to provide a dye in the presence of peroxidase and hydrogen peroxide (that is, compounds which react to provide a dye upon catalytic action of peroxidase).

In a preferred embodiment, the chlamydial or gonococcal antibody is not labeled, and detection of the antibody-antigen complex formed and bound to the support is accomplished using a second antibody (described below) which is specific to the unlabeled antibody and is appropriately labeled.

The chlamydial or gonococcal antibody can be contacted with the bound antigen in the presence of one or more proteins which reduce nonspecific interactions on the support. Useful proteins are well known and include, for example, casein, α-casein, fetal bovine serum and porcine gamma globulin. A particularly useful blocking composition comprises a protein and an amphoteric surfactant, as described and claimed in copending and commonly assigned U.S. Ser. No. 255,925 filed on even date herewith by Pronovost and entitled "Immunological Reagent Composition and Its Use in the Determination of Chlamydial or Gonococcal Antigens."

Once the bound antigen has been contacted with the chlamydial or gonococcal antibody, a bound immunological complex is formed on the support. To hasten the formation of this complex, the antibody and antigen are generally incubated at a temperature of from about 15° to about 30° C. for up to minutes. Preferably, the incubation is carried out at from about 18° to about 25° C. (that is, room temperature) for from 1 to 5 minutes. These mild incubation conditions are in sharp contrast to the 30 minutes at 37° C. described as necessary for adsorption of chlamydial antigen to bare supports in U.S. Pat. No. 4,497,899 (noted above).

After the incubation and within about 10 minutes of the antibody-antigen contact, the bound complex is washed one or more times with the wash solution of this invention which generally has a pH of from about 7 to about 12, and preferably of from about 9 to about 11.

The wash solution pH can be obtained by using certain bases or buffers depending upon the buffering capacity of the buffers. That is, the solution pH can be raised with base and maintained by a buffer, or certain strong buffers can be used to both raise and maintain the pH.

Buffers which can be present in the wash solution are readily known to one skilled in the art. Examples include alkali metal, alkaline earth and ammonium hydroxides (such as sodium hydroxide, potassium hydroxide and ammonium hydroxide), phosphates (such as trisodium phosphate and tripotassium phosphate), borates, 3-cyclohexylamino-1-propane sulfonic acid, 2-(N-cyclohexylamino)ethane sulfonic acid, 3-cyclohexylamino-2-hydroxy-1-propane sulfonic acid and others known in the art. The amount of buffer and base in the wash solution is chosen to provide suitable pH and buffering capability. Mixtures of buffers and bases can be used if desired.

The wash solution also contains one or more cationic surfactants. Particularly useful surfactants are cationic surfactants having quaternary ammonium salts, quaternary phosphonium salts, quaternary pyridinium salts and quaternary imidazolium salts or other cationic radicals within the molecule. Generally, any cationic surfactant is useful in the present invention as long as it does not adversely affect the bound antigen or immunological complexes on the solid support. Many cationic surfactants meeting those requirements are known in the art, and can be evaluated by routine experimentation. The standard resource of *McCutcheon's Emulsifiers and Detergents*, 1986 Edition, McCutcheon Division, Publishing Co., Glen Rock, N.J. 1986 can be consulted to find a number of useful cationic surfactants.

Representative surfactants include polypropoxy quaternary ammonium chlorides, acetates and phosphates (marketed as Emcol ® from Witco Chemical Co.), fatty acid amidoalkyldimethyl amines (Schercodines from Scher Chemical Co.), ethoxylated fatty amines (Pegameens from Borg-Warner Chemical Co.), long-chain alkyldiethanol methyl quaternary ammonium chlorides (M-Quat ® from Mazer Chemical Co.), fatty acid derivatives of imidazolines (Monazolines from Mona Industries), polyoxyethylene fatty amines (Mazeen ® from Mazer Chemical Co.), and long-chain alkylhydroxyethyl imidazolines (Alkazines from Alkaril Chemical Co.). Most useful surfactants are the quaternary ammonium salts of polypropoxy-t-amines (Emcol ® CC-9, CC-55 and CC-57 for example). The amount of cationic surfactant in the solution is generally at least about 0.1 weight percent. Preferably, it is present in an amount of from about 0.5 to about 3 weight percent. The amount may be adjusted for various surfactants to obtain the optimum results. A particularly useful wash solution is described below in reference to the examples.

In the embodiment described above where the chlamydial or gonococcal antibody is labeled, the assay procedure after washing is to detect the label directly or indirectly after addition of the appropriate reagents. This is done relatively quickly after washing the bound complex, that is generally within about 10 minutes, and preferably within about 1 to about 5 minutes. If desired, label detection can be hastened with incubation if the reagents warrant it. The label is then detected using standard equipment and procedures.

In a preferred embodiment, the chlamydial or gonococcal antibody is unlabeled, and after washing the bound complex, it is contacted with an antibody directed to the unlabeled antibody. This second antibody (that is, an anti-antibody) is appropriately labeled with any of the labels described above. The antibody can be monoclonal or polyclonal and either purchased or prepared using known techniques. In a chlamydial assay, the anti-antibody is preferably a polyclonal antibody which is reactive with either of the lipopolysaccharide or major outer membrane protein antibodies.

After this contact, the resulting labeled antigen-antibody-antibody complex which is bound to the support is incubated for up to about 10 minutes at a temperature of from about 15° to about 30° C., and preferably for about 1 to about 5 minutes at from 18° to 25° C.

Further washing can be carried out using the wash solution of this invention or any other suitable wash solution (for example, water or a buffer) to remove uncomplexed materials, and suitable enzyme substrates or other needed reagents are added to provide a detectable species. The bound labeled antigen-antibody-labeled antibody complex is then detected on the support using standard radiometric, colorimetric, fluorescent or other detection techniques.

A preferred method for the determination of chlamydial or gonococcal organisms comprises:

A. contacting chlamydial or gonococcal antigen extracted from a specimen suspected of containing chlamydial or gonococcal organisms, respectively, with a polymeric solid support so as to bind the antigen to the solid support, B. within about 10 minutes of the contact, contacting the bound antigen with an unlabeled chlamydial or gonococcal antibody so as to form an immunological complex bound to the support, C. within about 10 minutes of the antibody-antigen contact, separating uncomplexed materials from said bound immunological complex by washing the complex with the wash solution of this invention, D. contacting the bound complex with a labeled antibody to the unlabeled antibody so as to form a labeled antibody-antibody-antigen complex bound to the support, E. within about 10 minutes of the contact in step D, separating uncomplexed materials from the bound labeled complex by washing the labeled complex with the wash solution of this invention, and F. determining the presence of the labeled complex on the support as a measure of the amount of chlamydial or gonococcal organisms in the specimen.

In the preferred method just described, it is also possible to separate unbound antigen from bound antigen using the wash solution of this invention, if so desired.

The following examples are provided to illustrate, but not limit the scope of, the present invention.

To perform these examples, the mouse monoclonal antibody to the chlamydial lipopolysaccharide antigen was prepared using standard hybridoma technology and mouse cell line and stored in a solution of phosphate buffered saline (pH 7.4) containing 0.01% (by weight) azide. The antibody composition used in the assay was prepared by adding a sample (19 μl) of the antibody solution to a phosphate buffered saline solution (diluting 1:800) containing casein (0.5 weight %) and Lonzaine ® C amphoteric surfactant (0.01 weight %, available from Lonza, Inc.), then filtering through a 0.22 μmeter filter to obtain a working solution.

The labeled polyclonal antibody used was a goat anti-mouse IgG antibody conjugated to horseradish peroxidase (obtained from BioRad Laboratories). This conjugate was diluted to about 1:2000 in a phosphate buffered saline solution containing 0.5% (by weight) casein and 0.01% (by weight) Lonzaine® C, and filtered through a 0.22 μmeter filter to obtain a working solution.

An antigen extraction solution was prepared from the following components: sodium azide (25 mg in 25 ml), sodium chloride (2.5 ml of a 1.5 molar solution diluted to 25 ml), dithiothreitol reducing agent (29 mg in 25 ml), ethanolamine (6.25 ml of a 10% solution diluted to 25 ml), ethylenediaminetetraacetic acid (0.23 g in 25 ml) and sodium hydroxide (0.1 molar, pH adjusted to 12.5). To 15 ml of this solution was added 375 μl of a 10% (by weight) solution of Emcol® CC-36 cationic surfactant (quaternary ammonium chlorides of polypropoxy-t-amines, available from Witco Chemical) in methanol.

EXAMPLE 1

Determination of *Chlamydia trachomatis* Lipopolysaccharide Antigen Using Two Antibodies This example demonstrates the practice of the present invention using two antibodies, one directed against the lipopolysaccharide *C. trachomatis* antigen, and the second being labeled and directed to the chlamydial antibody.

The assay was carried out in a disposable test device designed similar to that described in copending and commonly assigned U.S. Ser. No. 19,810 (noted above). It contained a microporous membrane having quaternary ammonium groups on the surface (commercially available as the Pall Biodyne®-B membrane, Pall Corp.). Prior to use, the membrane was treated with Zonyl™ FSN (a nonionic fluorinated surfactant available from DuPont).

Chlamydial lipopolysaccharide antigen was extracted from elementary body protein (obtained from Professor W. J. Newhall of Indiana University) at about 20° C. for about 5 minutes using the extraction composition described above. Citrate (100 μliter of a 0.7 molar solution) was then added to lower the pH to about 7–8, followed by addition of a commercially available protease (for example, protease P0652 obtained from Sigma Chemical Co., 400 μl of a 2 mg/ml phosphate buffered saline solution). Extraction was continued for another 5 minutes at about 20° C., after which hydrogen peroxide and sodium hydroxide (pH above 10) were added to remove endogenous catalase, peroxidase and myeloperoxidase.

The treated specimen was then filtered through a 5 micrometer membrane to remove unwanted matter. The filtered extract (120 μl) was added to a test well of the disposable test device. Specimen fluid was allowed to flow through the membrane upon contact. Within a few seconds, all fluid had drained through the membrane and the monoclonal antibody solution described above was added to the test well and allowed to drain.

The immunological complex bound to the membrane was washed twice with a wash solution (160 μl) of this invention containing Emcol® CC-9 cationic surfactant (0.75 weight %) in phosphate buffered saline solution (pH 7.2).

Immediately after the second wash, the peroxidase-labeled polyclonal antibody solution (120 μl) described above was added to the test well, and the fluid allowed to drain through immediately. Incubation at about 20° C. was carried out again for about 5 minutes to form an antigen-antibody-labeled antibody complex ionically bound to the membrane.

After washing twice with the wash solution (160 μl) described above, a dye-providing composition (120 μl) was added to the test well. This composition included hydrogen peroxide (10 mmolar), 2-(4-hydroxy-3-methoxyphenyl)-4,5-bis(4-methoxyphenyl)imidazole leuco dye (0.005 weight %), poly(vinyl pyrrolidone)(1 weight %), 4'-hydroxyacetanilide (5 mmolar) and diethylene triaminepentaacetic acid (10 mmolar).

After about 5 minutes at room temperature, a red dye was observed in the test well indicating the presence of chlamydial antigen obtained from the specimen. The entire assay after extraction of antigen was performed in less than 30 minutes.

EXAMPLE 2

Determination of *Chlamydia trachomatis* Lipopolysaccharide Antigen Using One Antibody This example is similar to Example 1 except that only one antibody was used in the assay. This antibody was a peroxidase-labeled mouse monoclonal antibody to the lipopolysaccharide antigen of *C. trachomatis*. This labeled antibody was obtained using standard hybridoma technology.

The antigen was extracted from elementary body protein using a mixture of polyoxyethylene-9-lauryl ether (0.05% by weight, 80 μl), Zonyl™ FSN (1 weight %, 80 μl) and ethylenediaminetetraacetic acid (20 mmolar, 80 μl) in phosphate buffered saline solution. The saline solution volume varied from 560 μl for a buffered control solution (no antigen) to 510 μl for samples containing 5750 pg of antigen. Extraction was carried out for 10 minutes at 45° C., vortexed for 10 seconds and cooled to room temperature.

Posidyne® membranes in a disposable test device were prewet with polyoxyethylene-9-lauryl ether (0.005 weight %, 100 μl), Zonyl™ FSN (0.1 weight %) and ethylenediaminetetraacetic acid (2 mmmolar), then dried at 37° C. for 15 minutes.

The extracted antigen solutions (200 μl) having varying concentrations of antigen (288, 575, 1150, 2875 and 5750 pg) and the control solution were added to individual disposable devices, with fluid draining simultaneously.

A solution (200 μl) of peroxidase-labeled antibody conjugate, diluted 1:450 in commercially available instant nonfat dry milk (1 weight %), fetal bovine serum (1 weight %) in 0.05 molar phosphate buffered saline solution (pH 7.2) was added and the reaction mixture was incubated in the test device for 5 minutes at room temperature with fluid kept on top of the membrane by negative pressure. The fluid was then allowed to drain through the membrane.

A wash solution (500 μl) of this invention containing Emcol® CC-9 cationic surfactant (0.75 weight %) in phosphate buffered saline solution was added to the test devices and allowed to drain.

The leuco dye solution (50 μl) described above was added to the test devices with the fluid kept on the top of the membrane by negative pressure. After a few seconds, the fluid was allowed to drain and dye allowed to form.

After visual reading and grading of the dye density, a gradual increase in color was seen with an increase in the amount of antigen tested. No dye was observed in the control well.

EXAMPLES 3 and 4

Comparative Example

This example compares the use of the wash composition according to the present invention with the use of a wash composition of the prior art.

Materials

A wash composition of the present invention was prepared using the following materials: 3-(cyclohexylamino)-2-hydroxy-1-propane sulfonic acid (1.186 g) was dissolved in distilled water (100 ml), and the pH was raised to 10.0 by addition of 0.05 normal sodium hydroxide. Emcol TM CC-9 cationic surfactant (0.75 g) was added to the solution.

A test sample was used containing chlamydial elementary bodies (obtained as noted above) in a solution of bovine serum albumin in phosphate buffered saline solution (0.1 mg/ml). Final elementary body concentration was about 1000 pg.

A Control sample contained bovine serum albumin in phosphate buffered saline solution (0.1 mg/ml). That is, no chlamydial antigens were present.

An extraction device of the type described in U.S. Pat. No. 4,746,614 (noted above) was prepared containing a dried coating of tris(hydroxymethyl)aminomethane buffer (Sigma Chemical Co.) (20 μl of a 1.65 molar solution, pH 11.1) and thimerosal preservative (0.01 weight %).

Amideck TM protease (BioProducts Division, Eastman Kodak Co.) (4 mg/ml, 170 units/mg) was dissolved in 2-(N-morpholino)ethanesulfonic acid buffer (10 mmolar, pH 6.0) containing sodium chloride (50 mmolar), calcium chloride (5 mmolar), 1,2-propanediol (10% w/v) and preservative (0.01 weight %).

An extraction composition comprised: ethanolamine hydrochloride (0.47 molar), sodium chloride (0.27 molar) preservative (30 mmolar), ethylenediaminetetraacetic acid (50 mmolar) Emcol TM CC-36 cationic surfactant (0.45 volume %) and sodium hydroxide (0.66 normal) to raise the pH to 13.4.

A hydrogen peroxide wash solution contained hydrogen peroxide (12 volume %), diethylenetriaminepentaacetic acid (10 μmolar) and preservative (0.01 weight %).

The wash compositions used in the assays were:
Control A: 3-cyclohexylamino-2-hydroxy-1-propane sulfonic acid buffer (0.05 molar, pH 10.0),
Control B: phosphate buffered saline solution (pH 7.2),
Control C: phosphate buffered saline solution and Tween TM 20 nonionic surfactant (0.75 weight %),
Example 3: phosphate buffered saline solution and Emcol TM CC-9 cationic surfactant (0.75 weight %), and
Example 4: 2-cyclohexylamino-2-hydroxy-1-propane sulfonic acid buffer (0.05 molar, pH 10.0) and Emcol TM CC-9 cationic surfactant (0.75 weight %).

A Control reagent composition comprised antibodies to creatine kinase-MB (5 μg/ml), casein (0.5 weight %), Lonzaine TM C amphoteric surfactant (0.01 weight %) and preservative (0.01 weight %) in phosphate buffered saline solution (pH 7.2).

Monoclonal antibodies to the chlamydial lipopolysaccharide antigen (4 μg/ml) were supplied with the casein, amphoteric surfactant and preservative noted above for the Control composition.

Goat polyclonal anti-mouse IgG antibodies conjugated to horseradish peroxidase (from BioRad, 1:700 dilution) were supplied in a composition with casein (0.5 weight %), Lonzaine TM C amphoteric surfactant (0.1 weight %), 4'-hydroxyacetanilide (10 mmolar) and preservative (0.01 weight %) in phosphate buffered saline solution (pH 7.2).

A leuco dye composition was prepared using 2-(4-hydroxy-3-methoxyphenyl)-4,5-bis(4-methoxyphenyl)imidazole leuco dye (0.008 weight %), poly(vinylpyrrolidone)(1 weight %), sodium phosphate (10 mmolar, pH 6.8) diethylenetriaminepentaacetic acid (10 μmolar), 4'-hydroxyacetanilide (2 mmolar) and hydrogen peroxide (10 mmolar).

Assay

The protease solution (280 μl) was added to the extraction device, followed by addition of a solution (50 μl) containing diethiothreitol (0.188 molar) and poly(acrylamide)(6.35 weight %), followed by the test sample (12.5 μl). A side-by-side comparison was made with the Control sample (12.5 μl) using separate extraction and test devices. The resulting solutions in the extraction devices were mixed and incubated at room temperature for 3 minutes.

The extraction solution (280 μl) noted above was then added to the extraction device, mixed and incubated at room temperature for 3 minutes. Then, the hydrogen peroxide solution (280 μl) was also added, mixed and incubated at room temperature for 3 minutes.

Portions (160 μl) of the solution in the extraction device were added to each of three wells of a disposable test device as described herein. The first well was considered a Control well, and the other two were considered test wells.

Fluid was allowed to drain through the membrane in each well, and the wells were then washed twice each with the wash compositions noted above allowing the fluids to drain.

The Control reagent composition noted above (80 μl) was added to each Control well, and the chlamydial antibody composition (80 μl) was added to the test wells without drainage. Incubation at room temperature was carried out for 2 minutes.

Fluid was allowed to drain and the wells were washed twice again. Then, the anti-antibody composition (80 μl) was added to each well, followed by incubation at room temperature for 5 minutes.

After another wash step, the leuco dye composition (80 μl) to each well. Incubation at room temperature for 5 minutes was carried out and reaction was stopped by adding a sodium azide solution (0.01 weight %, 120 μl). The dye density on the membranes was measured and converted to transmission density ($D_T$). The results are shown in the Table below. They show that the wash compositions of the present invention provide the desired low background and improved sensitivity. Example 4 provides the lowest background and highest sensitivity because it used a higher pH wash composition.

TABLE

| Wash Compositions | $D_T$ | | | | | |
|---|---|---|---|---|---|---|
| | 1000 pg Antigen | | | Control (no Antigen) | | |
| | Control Well | Test Well #1 | Test Well #2 | Control Well | Test Well #1 | Test Well #2 |
| Control A | 0.014 | 0.102 | 0.094 | 0.018 | 0.015 | 0.012 |
| Control B | 0.016 | 0.106 | 0.114 | 0.021 | 0.014 | 0.023 |
| Control C | 0.015 | 0.055 | 0.056 | 0.013 | 0.015 | 0.011 |
| Example 3 | 0.018 | 0.114 | 0.120 | 0.019 | 0.013 | 0.019 |
| Example 4 | 0.009 | 0.113 | 0.117 | 0.011 | 0.008 | 0.009 |

The invention has been described in detail with particular reference to preferred embodiments thereof, but it will be understood that variations and modifications can be effected within the spirit and scope of the invention.

I claim:

1. A wash solution for washing an antigen-antibody complex in an immunoassay, said wash solution having a pH of from about 9 to about 11 and consisting essentially of from about 0.1 to about 3 weight percent of one or more cationic surfactants, at least one of said cationic surfactants including one or more quaternary ammonium salts of a polypropoxy-t-amine.

2. The wash solution of claim 1 containing the buffer 3-cyclohexylamino-2-hydroxy-1-propane sulfonic acid.

3. The wash solution of claim 1 wherein said cationic surfactant is present in an amount of from about 0.5 to about 3 weight percent.

* * * * *